US009867594B2

(12) United States Patent
Hayashi et al.

(10) Patent No.: US 9,867,594 B2
(45) Date of Patent: Jan. 16, 2018

(54) ULTRASONIC MEASUREMENT APPARATUS, ULTRASONIC IMAGE APPARATUS, AND ULTRASONIC MEASUREMENT METHOD

(71) Applicant: SEIKO EPSON CORPORATION, Tokyo (JP)

(72) Inventors: Masaki Hayashi, Nagano (JP); Ryoki Watanabe, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 27 days.

(21) Appl. No.: 14/470,397

(22) Filed: Aug. 27, 2014

(65) Prior Publication Data
US 2015/0073277 A1   Mar. 12, 2015

(30) Foreign Application Priority Data

Sep. 10, 2013 (JP) .................................. 2013-187152
Jul. 3, 2014 (JP) .................................. 2014-137454

(51) Int. Cl.
*G01S 15/00* (2006.01)
*A61B 8/08* (2006.01)
(Continued)

(52) U.S. Cl.
CPC ............ *A61B 8/5207* (2013.01); *A61B 8/145* (2013.01); *A61B 8/4427* (2013.01);
(Continued)

(58) Field of Classification Search
CPC .................................................. A61B 8/5207
See application file for complete search history.

(56) References Cited

U.S. PATENT DOCUMENTS 5,980,459 A * 11/1999 Chiao ...................... A61B 8/06
                                                                  600/447
6,210,334 B1 * 4/2001 Phillips .................... A61B 8/06
                                                                  600/453
(Continued)

FOREIGN PATENT DOCUMENTS

JP        2012-170826 A      9/2012

OTHER PUBLICATIONS

Johan-Fredrik Synnevag, "Adaptive Beamforming Applied to Medical Ultrasound Imaging", IEEE Transactions on ultrasonics, ferroelectrics, and frequency control, vol. 54, No. 8, 2007.*
(Continued)

*Primary Examiner* — Tse Chen
*Assistant Examiner* — Joanne Hoffman
(74) *Attorney, Agent, or Firm* — Global IP Counselors, LLP

(57) ABSTRACT

An ultrasonic measurement apparatus includes a reception processing unit, a harmonic processing unit, a signal processing unit and an image generation unit. The reception processing unit is configured to receive, as a received signal, an ultrasonic echo corresponding to an ultrasonic wave transmitted toward a subject. The harmonic processing unit is configured to extract a harmonic component of the ultrasonic echo from the received signal. The signal processing unit is configured to add a weighting to the harmonic component by using a weight that varies depending on a value of the harmonic component. The image generation unit is configured to generate an image based on a signal to which the weighting has been added.

11 Claims, 13 Drawing Sheets

(51) Int. Cl.
*G01S 7/52* (2006.01)
*G01S 15/89* (2006.01)
*G10K 11/34* (2006.01)
*A61B 8/14* (2006.01)
*A61B 8/00* (2006.01)
*B06B 1/06* (2006.01)

(52) U.S. Cl.
CPC ............ *A61B 8/4494* (2013.01); *A61B 8/461* (2013.01); *A61B 8/462* (2013.01); *A61B 8/5269* (2013.01); *G01S 7/52038* (2013.01); *G01S 7/52047* (2013.01); *G01S 15/8915* (2013.01); *G01S 15/8925* (2013.01); *G01S 15/8927* (2013.01); *G10K 11/346* (2013.01); *B06B 1/0603* (2013.01); *G01S 7/52085* (2013.01)

(56) References Cited

U.S. PATENT DOCUMENTS

| | | | |
|---|---|---|---|
| 6,511,426 B1* | 1/2003 | Hossack | A61B 8/483 600/437 |
| 6,632,177 B1* | 10/2003 | Phillips | A61B 8/481 600/458 |
| 2001/0014773 A1* | 8/2001 | Jago | G01S 7/52036 600/437 |
| 2001/0053489 A1* | 12/2001 | Dirksen | G03F 7/70241 430/30 |
| 2002/0028994 A1* | 3/2002 | Kamiyama | A61B 8/463 600/437 |
| 2003/0071750 A1* | 4/2003 | Benitz | G01S 13/9011 342/25 R |
| 2009/0036772 A1* | 2/2009 | Lu | G01S 7/52046 600/437 |
| 2010/0246326 A1* | 9/2010 | Ichigo | G01N 29/12 367/93 |
| 2012/0212618 A1 | 8/2012 | Park et al. | |
| 2015/0025385 A1* | 1/2015 | Ikeda | A61B 8/5207 600/443 |

OTHER PUBLICATIONS

Vijay Madisetti, The Digital Signal Processing Handbook, 6.8, 1998.*

Texas Instruments, White Paper, "Signal Processing Overview of Ultrasound Systems for Medical Imaging", 2008.*

Iben Kraglund Holfort, Fredrik Gran, and Jurgen Arendt Jensen, "Broadband Minimum Variance Beamforming for Ultrasound Imaging", IEEE Transactions on Ultrasonics, Ferroelectrics, and Frequency Control, vol. 56, No. 2, Feb. 2009.*

Babak Mohammadzadeh Asl, and Ali Mahloojifar, "Eigenspace-Based Minimum Variance Beamforming Applied to Medical Ultrasound Imaging", IEEE Transactions on Ultrasonics, Ferroelectrics, and Frequency Control, vol. 57, No. 11, Nov. 2010.*

Sven Peter Nasholm et al: "Capon beamforming applied to second-harmonic ultrasound experimental data", 2011 IEEE International Ultrasonics Symposium(IUS), Oct. 18, 2011; pp. 2217-2220.

J-F Synnevag et al:"Adaptive Beamforming Applied to Medical Ultrasound Imaging", IEEE Transactions on Ultrasonics, Ferroelectrics and Frequency Control, vol. 54, No. 8; Aug. 1, 2007; pp. 1606-1613.

Averkiou M A: "Tissue harmonic imaging", Proceedings of 2000 IEEE Ultrasonics Symposium, vol. 2; Oct. 22, 2000; pp. 1563-1572.

* cited by examiner

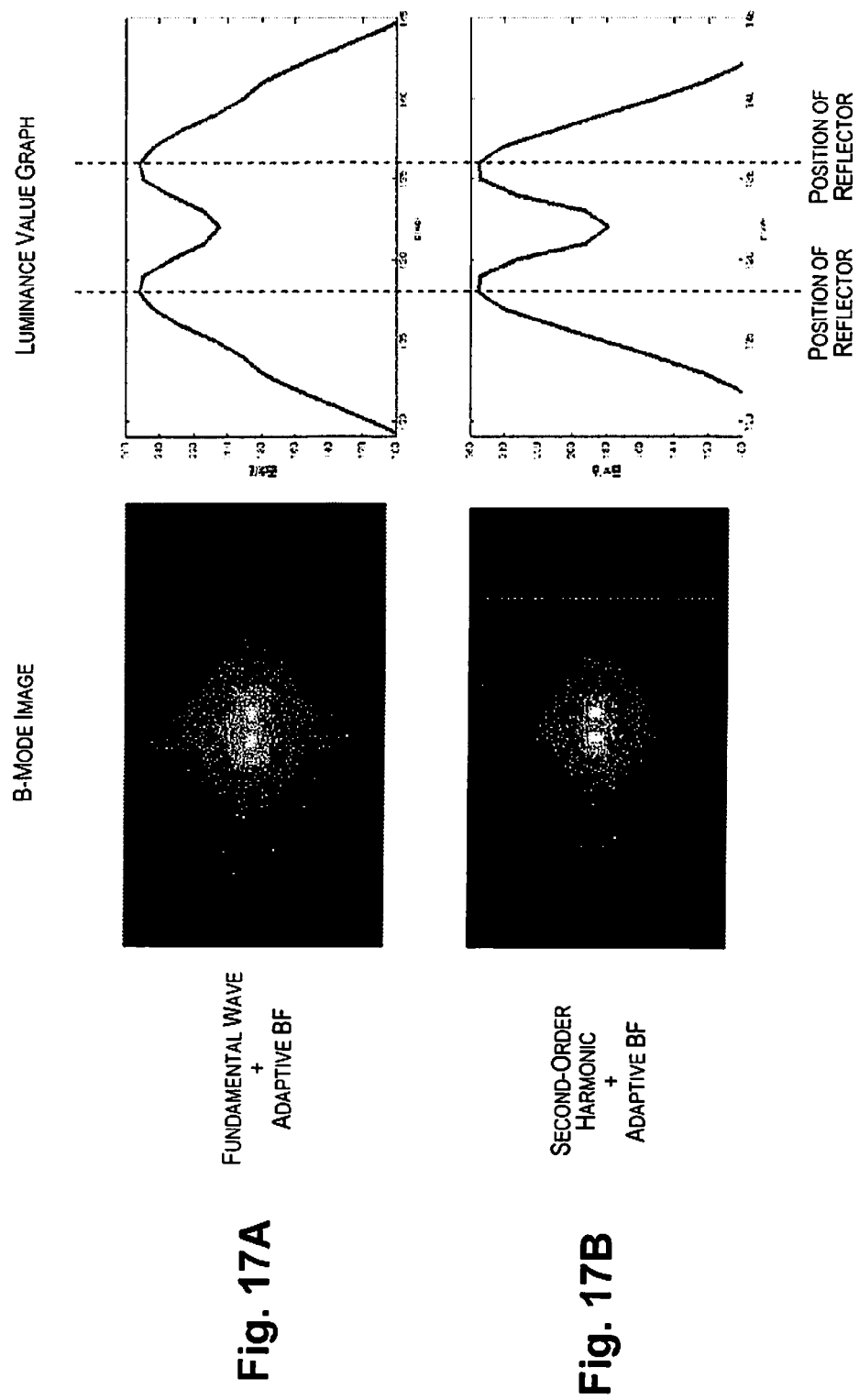

ULTRASONIC MEASUREMENT APPARATUS, ULTRASONIC IMAGE APPARATUS, AND ULTRASONIC MEASUREMENT METHOD

CROSS-REFERENCE TO RELATED APPLICATIONS

This application claims priority to Japanese Patent Application No. 2013-187152 filed on Sep. 10, 2013, and Japanese Patent Application No. 2014-137454 filed on Jul. 3, 2014. The entire disclosures of Japanese Patent Application Nos. 2013-187152 and 2014-137454 are hereby incorporated herein by reference.

BACKGROUND

Technical Field

The present invention relates to an ultrasonic measurement apparatus, an ultrasonic image apparatus, and an ultrasonic measurement method.

Related Art

A known feature in an ultrasonic measurement apparatus is one where a component of a transmitted fundamental frequency is extracted from an ultrasonic echo for ultrasonic waves of the fundamental frequency, and the extracted component is subjected to adaptive beamforming. Adaptive beamforming is able to maximize the sensitivity of received waves coming from a desired direction, or to minimize the sensitivity of unneeded waves coming from a direction other than a desired direction, and therefore has been put to practical use in, for example, radar systems and submarine sonar systems.

As one example of adaptive beamforming, Japanese laid-open patent publication 2012-170826 discloses an ultrasonic beamforming method for splitting an inputted ultrasonic signal into a plurality of regions over an observation space, calculating a weighting value by region, calculating a pixel weighting value for each pixel, and calculating a beamforming value.

SUMMARY

However, practical problems still emerge when the adaptive beamforming described above is directly applied without alteration to such an ultrasonic measurement apparatus as would be for capturing biological images.

For example, in the case of radar systems, even though there are distant aircraft and mountains, there are no objects such as would reflect large amounts of radio waves in the midway spaces. In submarine sonar apparatuses, as well, the ultrasonic waves are being propagated through seawater and therefore no strong reflectors are found there. In the case of an ultrasonic measurement apparatus, however, though an attempt may be being made to acquire an ultrasonic echo coming from a specific organ, tumor, or the like inside the body, there are numerous other organs, fat, muscle, blood vessel walls, and the like present as reflectors of ultrasonic waves in the periphery of that specific organ or the like and in the space from the probe to that specific organ or the like. Therefore, an image with high resolution can only be obtained when the acoustic impedance of each of the reflectors is identified and imaged. Other problems specific to an ultrasonic measurement apparatus include artifacts, which are virtual images caused by multiple reflection and diffraction of the ultrasonic waves inside the body.

As such, even when the adaptive beamforming technique described above is applied to an ultrasonic measurement apparatus, not only are there the concerns that it could become extremely difficult to differentiate the unneeded waves and that calculation processes could become more complex, but also the calculations themselves might no longer converge. As a result, it becomes impossible to obtain an image with high resolution.

The present invention has been made in view of such circumstances, and has the purpose of providing a feature whereby an image with higher resolution is obtained even while adaptive beamforming is being applied to an ultrasonic measurement apparatus.

An ultrasonic measurement apparatus according to one aspect includes a reception processing unit, a harmonic processing unit, a signal processing unit and an image generation unit. The reception processing unit is configured to receive, as a received signal, an ultrasonic echo corresponding to an ultrasonic wave transmitted toward a subject. The harmonic processing unit is configured to extract a harmonic component of the ultrasonic echo from the received signal. The signal processing unit is configured to add a weighting to the harmonic component by using a weight that varies depending on a value of the harmonic component. The image generation unit is configured to generate an image based on a signal to which the weighting has been added. According to this aspect, a weighting addition process is applied, which uses different weights depending on a value of the harmonic component that has been extracted in the harmonic processing to add a weighting to the harmonic component that has been extracted in the harmonic processing. This makes it possible to obtain an image with enhanced azimuth (lateral) resolution.

In the ultrasonic measurement apparatus according to the above aspect, the reception processing unit is preferably configured to receive the ultrasonic echo via an ultrasonic element array having a plurality of channels, as the received signal of each of the channels, the harmonic processing unit is preferably configured to extract the harmonic component from the received signal of each of channels, and the signal processing unit is preferably configured to cause the weight for each of the channels to vary depending on the value of the harmonic component of each of the channels and to add the weighting to the harmonic component of each of the channels using the weight. This makes it possible to obtain an image with more enhanced azimuth resolution.

In the ultrasonic measurement apparatus according to the above aspect, the signal processing unit is preferably configured to perform a delay process corresponding to each of the channels on the harmonic component of each of the channels, and to cause the weight of each of the channels to vary depending on the value of the harmonic component of each of the channels after the delay processing. This makes it possible to align the phases of the harmonic components of each of the channels and therefore makes it possible to obtain an image with enhanced accuracy of the calculation of weight and the weighting addition as well as further enhanced azimuth resolution.

In the ultrasonic measurement apparatus according to the above aspect, the signal processing unit is preferably configured to perform a spatial averaging process by taking a plurality of sub-apertures out from a plurality of apertures constituted of the channels to determine the weight of each of the channels used to add the weighting to the harmonic component of each of the channels after the delay processing. This makes it possible to obtain an image with improved azimuth estimation accuracy and more enhanced azimuth resolution.

The ultrasonic measurement apparatus according to the above aspect preferably further includes a filter processing unit configured to remove noise by performing a filter process on one of the received signal of each of the channels and the harmonic component of each of the channels. This makes it possible to obtain an image from which noise has been removed and resolution has been enhanced more.

In the ultrasonic measurement apparatus according to the above aspect, the reception processing unit is preferably configured to receive, as received signals, the ultrasonic echo corresponding to two ultrasonic waves transmitted toward the subject with the two ultrasonic waves having a phase difference of 180° at a predetermined frequency, and the harmonic processing unit is preferably configured to extract the harmonic component by adding the received signals of the ultrasonic echo corresponding to the two ultrasonic waves. This further reduces any overlap between the harmonic component and other components such as the fundamental wave component, and therefore makes broadband receiving possible and makes it possible to improve the distance resolution.

In the ultrasonic measurement apparatus according to the above aspect, the harmonic processing unit is preferably configured to extract the harmonic component by performing a filter process. This makes it possible to reduce the number of iterations of receiving the ultrasonic waves for the purpose of extracting the harmonic component and to enhance the time resolution (frame rate).

An ultrasonic image apparatus according to another aspect includes a reception processing unit, a harmonic processing unit, a signal processing unit, an image generation unit and a display unit. The reception processing unit is configured to receive, as a received signal, an ultrasonic echo corresponding to an ultrasonic wave transmitted toward a subject. The harmonic processing unit is configured to extract a harmonic component of the ultrasonic echo from the received signal. The signal processing unit is configured to add a weighting to the harmonic component by using a weight that varies depending on a value of the harmonic component. The image generation unit is configured to generate an image based on a signal to which the weighting has been added. The display unit is configured to display the image that has been generated. This makes it possible to obtain an image with more enhanced azimuth resolution.

An ultrasonic measurement method according to another aspect includes: receiving, as a received signal, an ultrasonic echo corresponding to an ultrasonic wave transmitted toward a subject; extracting a harmonic component of the ultrasonic echo from the received signal; adding a weighting to the harmonic component by using a weight that varies depending on a value of the harmonic component; and generating an image based on a signal to which the weighting has been added. This makes it possible to obtain an image with more enhanced azimuth resolution.

BRIEF DESCRIPTION OF THE DRAWINGS

Referring now to the attached drawings which form a part of this original disclosure:

FIG. 4A illustrates a case where there are four columns of elements and FIG. 4B illustrates a case where there is one column of elements;

FIGS. 17A and 17B are drawings describing a (second) result of a simulation relating to the display of a B-mode image.

DETAILED DESCRIPTION OF EXEMPLARY EMBODIMENTS

An embodiment of the present invention shall be described below with reference to the accompanying drawings.

Figure 1:
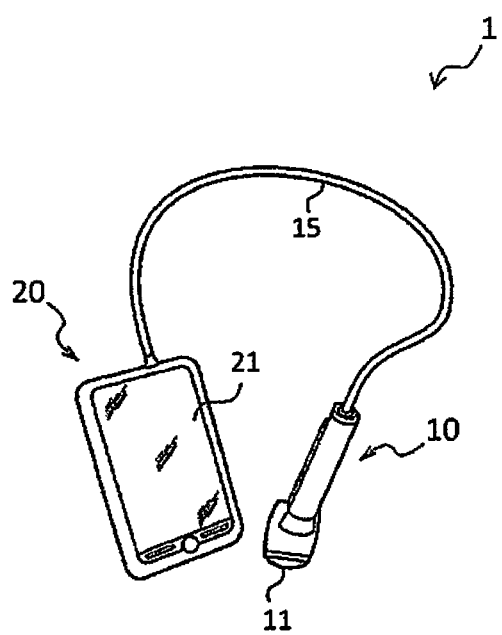
FIG. 1 is a drawing illustrating one example of the outer appearance of an ultrasonic image apparatus as in an embodiment of the present invention.

FIG. 1 is a drawing illustrating one example of the outer appearance of an ultrasonic image apparatus as in an embodiment of the present invention. An ultrasonic image apparatus 1 is, for example, a handheld apparatus, and has an ultrasonic probe 10 and an ultrasonic image apparatus main body 20. The ultrasonic probe 10 and the ultrasonic image apparatus main body 20 are connected by a cable 15. The ultrasonic image apparatus 1 is not, however, limited to being handheld, but rather may be, for example, a stationary type or an integral type, which is where the ultrasonic probe is built into an apparatus main body.

The ultrasonic probe 10 has an ultrasonic transducer device 11. The ultrasonic transducer device 11 both transmits an ultrasonic beam at a subject and receives an ultrasonic echo created by the ultrasonic beam, while also scanning over the subject along a scan plane.

Taking the example of a type where piezoelectric elements are used, the ultrasonic transducer device 11 has a plurality of ultrasonic transducer elements 12 (an ultrasonic element array; see FIG. 2, etc.) and a substrate on which a plurality of apertures are arranged in the form of an array.

FIG. 2 illustrates one example of the configuration of an ultrasonic transducer element. In the present embodiment, a monomorph (unimorph) with which a thin piezoelectric element and a metal place (vibrating film) are bonded together is employed as the ultrasonic transducer element 12.

Figure 2A:
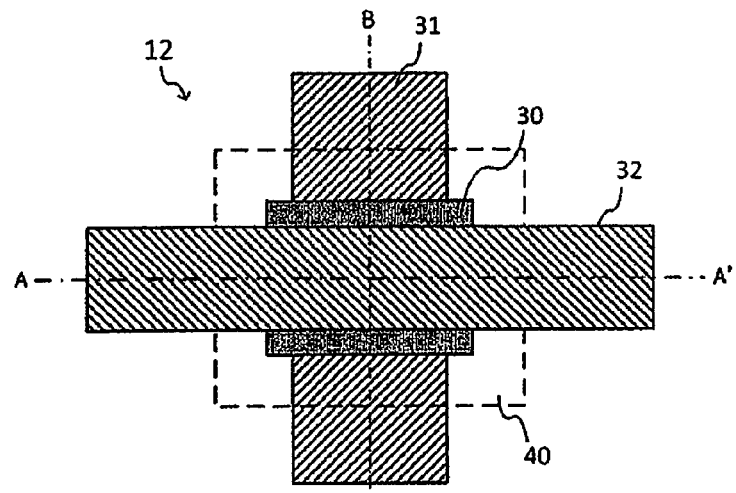
FIGS. 2A to 2C are drawings illustrating one example of the configuration of an ultrasonic transducer element.
Figure 2B:
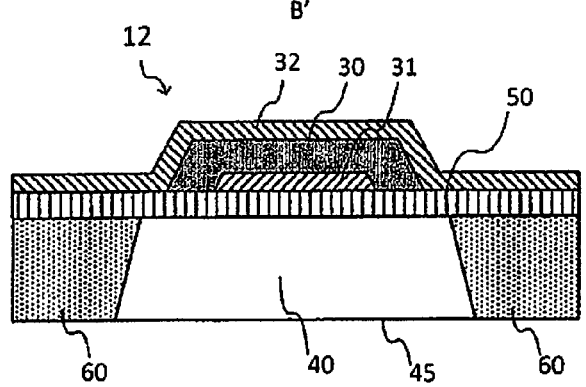
Figure 2C:
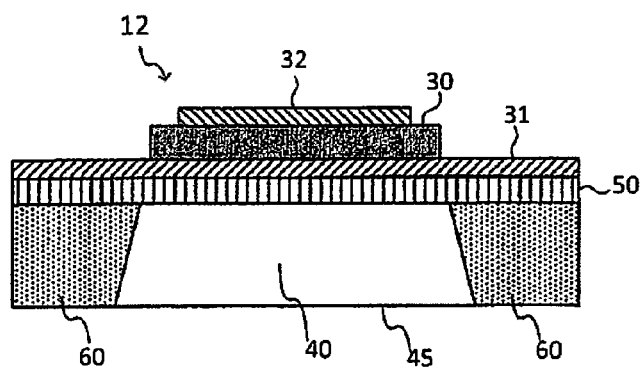

FIG. 2A is a plan view, seen from a direction perpendicular to an element formation surface-side substrate (silicon substrate) 60, of an ultrasonic transducer element 12 formed on the substrate 60. FIG. 2B is a cross-sectional view taken along the A-A' line in FIG. 2A. FIG. 2C is a cross-sectional view taken along the B-B' line in FIG. 2A.

The ultrasonic transducer element 12 has a piezoelectric element section and a vibrating film (membrane, support member 50. The piezoelectric element section has a piezoelectric layer (piezoelectric film) 30, a first electrode layer (lower electrode) 31, and a second electrode layer (upper electrode) 32.

The piezoelectric layer 30 is formed of, for example, lead zirconium titanate (PZT), and is provided so as to cover at least a part of the first electrode layer 31. The material of the piezoelectric layer 30 is not intended to be limited to being PZT; rather, for example, lead titanate (PbTiO3), lead zirconate (PbZrO3), lead lanthanum titanate ((Pb,La)TiO3), or the like may be used.

The first electrode layer 31 is formed of, for example, a metal thin-film on an upper layer of the vibrating film 50. This first electrode layer 31 may be a wiring that extends to the outside of an element formation region and is connected to an adjacent ultrasonic transducer element 12, as illustrated in FIG. 2A.

The second electrode layer 32 is formed of, for example, a metal thin-film and is provided so as to cover at least a part of the piezoelectric layer 30. This second electrode layer 32 may be a wiring that extends to the outside of the element formation region and is connected to an adjacent ultrasonic transducer element 12, as illustrated in FIG. 2A.

A lower electrode (first electrode) of the ultrasonic transducer element 12 is formed of the first electrode layer 31, and an upper electrode (second electrode) is formed of the second electrode layer 32. More specifically, a portion of the first electrode layer 31 that is covered by the piezoelectric layer 30 forms the lower electrode, and a portion of the second electrode layer 32 that covers the piezoelectric layer 30 forms the upper electrode. That is to say, the piezoelectric layer 30 is provided so as to be sandwiched between the lower electrode and the upper electrode.

An aperture 40 is formed by using a reactive ion etching (RIE) or the like to etch from a reverse surface (surface on which the elements are not formed) side of the substrate 60 (silicon substrate). The resonant frequency of the ultrasonic waves is determined by the size of this aperture 40, and the ultrasonic waves thereof are emitted from the piezoelectric layer 30 side (the front direction from the back of the page in FIG. 2A).

The vibrating film (membrane) 50 is provided so that the aperture 40 is covered by, for example, a double-layered structure of an SiO2 thin-film and a ZrO2 thin-film. This vibrating film 50 supports the first and second electrode layers 31, 32 of the piezoelectric layer 30, and vibrates and generates ultrasonic waves in accordance with expansion and contraction of the piezoelectric layer 30.

Figure 3:
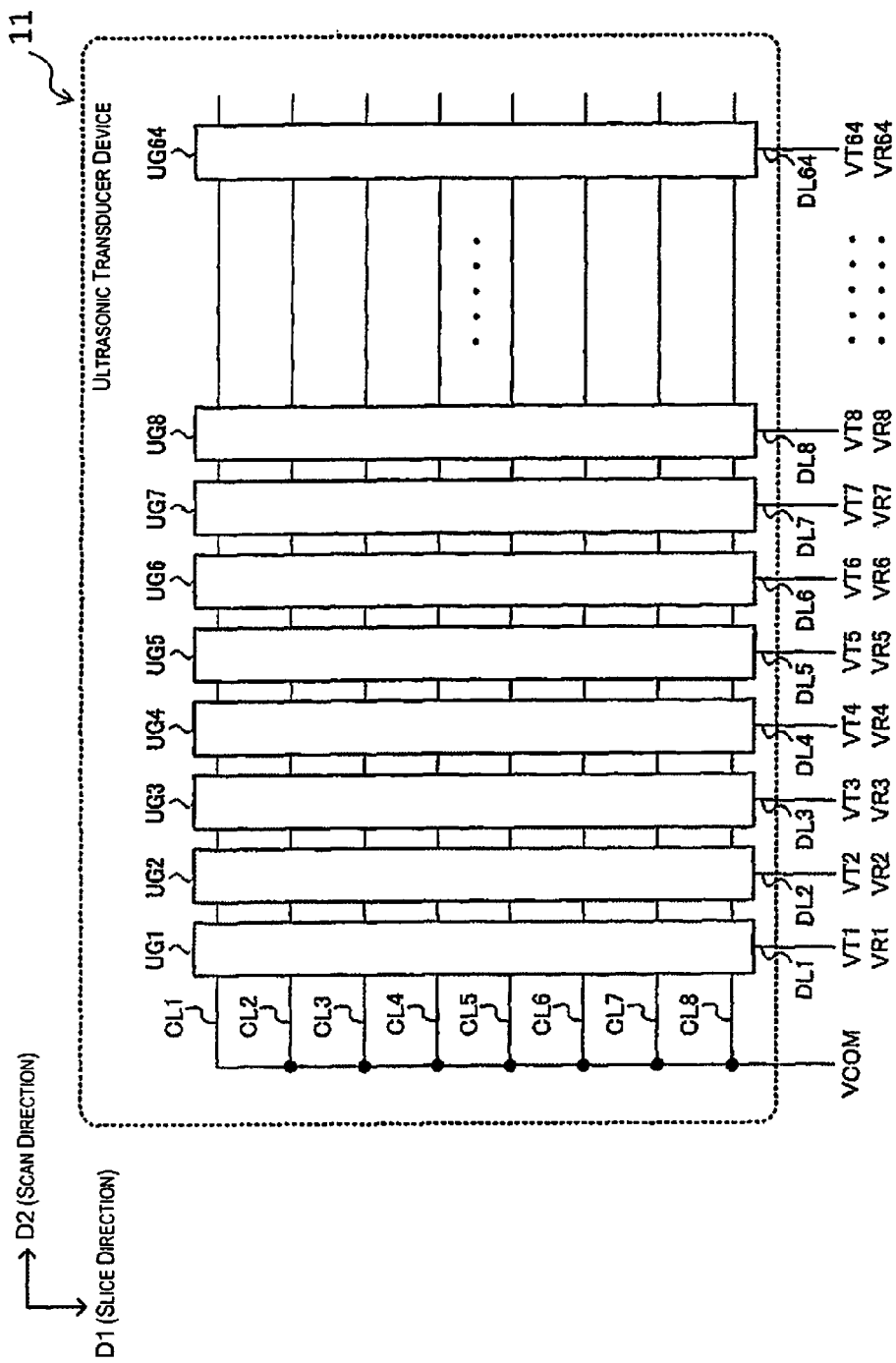
FIG. 3 is a drawing illustrating one example of the configuration of an ultrasonic transducer device (an element chip)

FIG. 3 illustrates one example of the configuration of an ultrasonic transducer device (element chip). The ultrasonic transducer device 11 of the present configuration example comprises pluralities of ultrasonic transducer element groups UG1 to UG64, drive electrode lines DL1 to DL64 (more broadly, a first through m-th drive electrode line, where n is an integer 2 or higher), and common electrode lines CL1 to CL8 (more broadly, a first through n-th common electrode line, where m is an integer 2 or higher). The number (m) of drive electrode lines is not limited to the number illustrated in FIG. 3, nor is the number (n) of common electrode lines.

The plurality of ultrasonic transducer element groups UG1 to UG64 are arranged in 64 columns along a second direction D2 (a scan direction). Each of the ultrasonic transducer element groups in UG1 to UG64 has a plurality of ultrasonic transducer elements, which are arranged along a first direction D1 (slice direction).

Figure 4A:
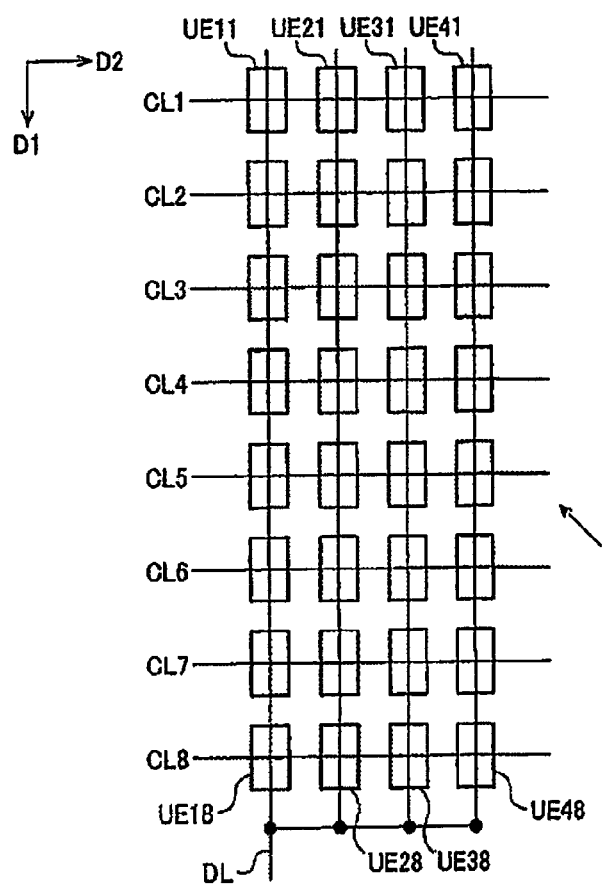
FIGS. 4A and 4B are drawings illustrating one example of the configuration of an ultrasonic transducer element group UG (UG1 to UG64), where

FIG. 4A illustrates an example of an ultrasonic transducer element group UG (UG1 to UG64). In FIG. 4A, the ultrasonic transducer element group UG is constituted of a first through fourth element column. The first element column is constituted of ultrasonic transducer elements UE11 to UE18 arranged along the first direction D1, and the second element column is constituted of ultrasonic transducer elements UE21 to U28 arranged along the first direction D1. The same is true of the third element column (UE31 to UE38) and the fourth element column (UE41 to UE48). The drive electrode line DL (DL1 to DL64) has common connections to these first through fourth element columns. Also, the common electrode lines CL1 to CL8 are connected to the ultrasonic transducer elements of the first through fourth element columns.

Figure 4B:
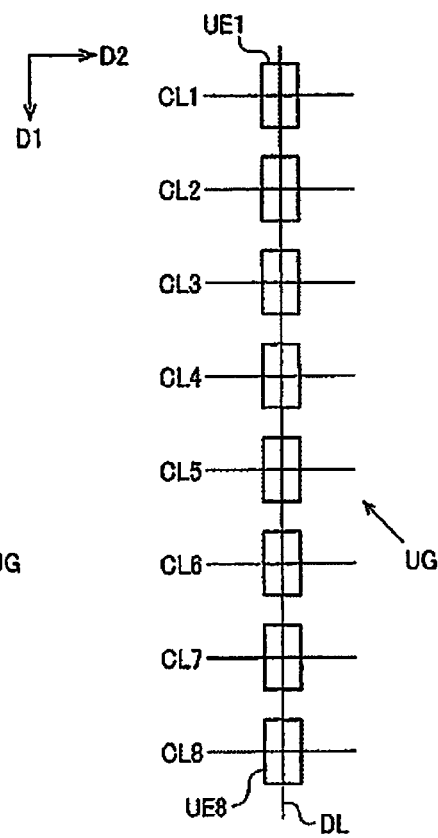

The ultrasonic transducer element group UG in FIG. 4A constitutes one channel of the ultrasonic transducer device. That is to say, the drive electrode line DL corresponds to the drive electrode line of one channel, and a transmitted signal of one channel from a transmission circuit is inputted to the drive electrode line DL. A received signal of one channel from the drive electrode line DL is outputted from the drive electrode line DL. The number of element columns that constitute one channel is not limited to being four columns, such as is illustrated in FIG. 4A, but rather may be fewer than four columns or may be more than four columns. For example, the number of element columns may be one column, as illustrated in FIG. 4B.

The description now relates again to FIG. 3. The drive electrode lines DL1 to DL64 (first through m-th drive electrode lines) are wired along the first direction D1. An i-th (where i is an integer 1≤i≤m) drive electrode line DLi (an i-th channel) out of the drive electrode lines DL1 to DL64 is wired to the first electrodes (for example, the lower electrodes) of the ultrasonic transducer elements of the i-th ultrasonic transducer element group UGi.

During a transmission period where ultrasonic waves are emitted, transmitted signals VT1 to VT64 are supplied to the ultrasonic transducer elements via the drive electrode lines DL1 to DL64. During a reception period where an ultrasonic echo signals are received, received signals VR1 to VR64 from the ultrasonic transducer elements are outputted via the drive electrode lines DL1 to DL64.

The common electrode lines CL1 to CL8 (first through n-th common electrode lines) are wired along the second direction D2. The second electrodes of the ultrasonic transducer elements are connected to one of the common electrode lines CL1 to CL8. More specifically, as per the example illustrated in FIG. 3, a j-th (where j is an integer 1≤j≤n) common electrode line CLj out of the common electrode lines CL1 to CL8 is connected to the second electrodes (for example, the upper electrodes) of the ultrasonic transducer elements arranged in a j-th row.

A common voltage VCOM is supplied to the common electrode lines CL1 to CL8. The common voltage VCOM should be a constant direct current voltage, and need not be 0 V, i.e., a ground potential.

In the transmission period, a voltage that is the difference between a transmitted signal voltage and the common voltage is applied to the ultrasonic transducer elements, and ultrasonic waves of a predetermined frequency are emitted.

The arrangement of the ultrasonic transducer elements, however, is not limited to being the matrix arrangement illustrated in FIG. 3, but rather may be, inter alia, a so-called staggered arrangement where the elements of two adjacent columns are arranged in an alternately zigzagging manner. Furthermore, though FIGS. 4A and 4B illustrate a case where one transducer element is used both as a transmitter element and a receiver element, the present embodiment is not limited thereto. For example, ultrasonic transducer elements for transmitter elements and ultrasonic transducer elements for receiver elements may be separated provided and arranged in an array.

The ultrasonic transducer elements 12 also are not limited to being a form where piezoelectric elements are used. For example, transducers using capacitive elements such as capacitive micro-machined ultrasonic transducers (c-MUTs) may be employed, or bulk-type transducers may be employed.

The description now relates again to FIG. 1. Provided to the ultrasonic image apparatus main body 20 is a display unit 21. The display unit 21 displays displayed image data generated by a control unit 22 (see FIG. 5) provided to inside the ultrasonic image apparatus main body 20. For example, a display apparatus such as a liquid crystal display, an organic EL display, or an electronic paper could be used for the display unit 21.

Figure 5:
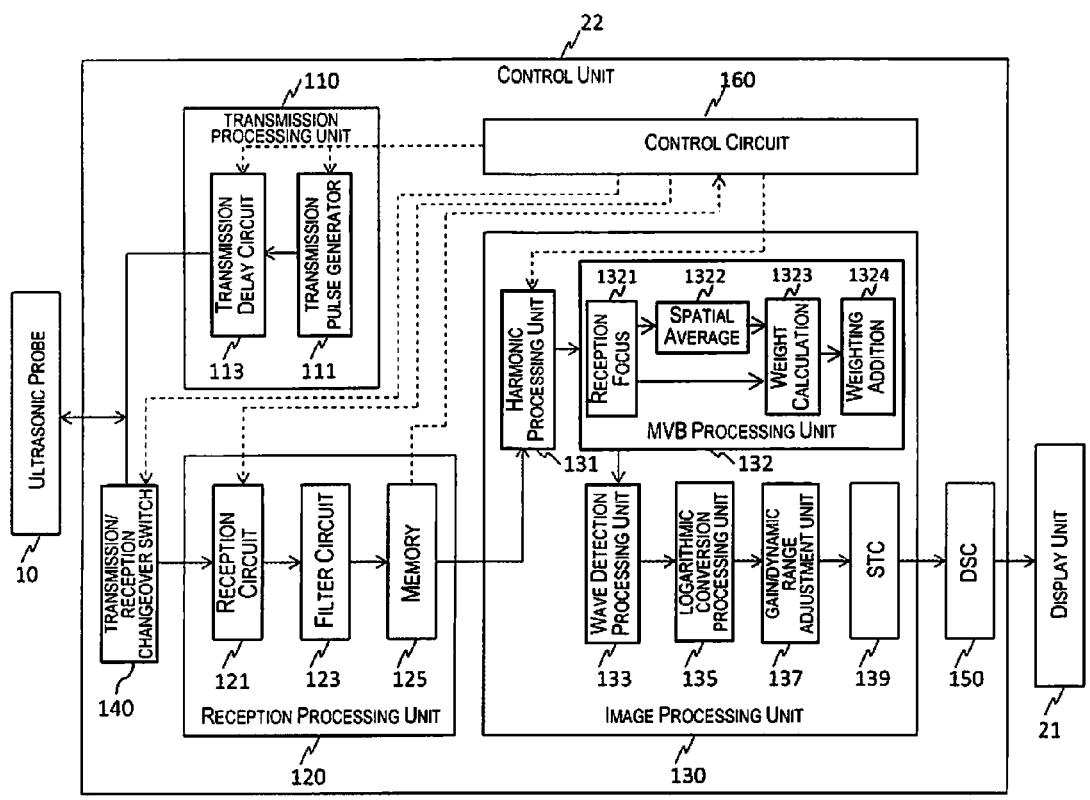
FIG. 5 is a block diagram illustrating one example of a functional configuration of a control unit.

FIG. 5 is a block diagram illustrating one example of the functional configuration of the control unit 22. The control unit 22 has a transmission process unit 110, a reception processing unit 120, an image processing unit 130, a transmission/reception changeover switch 140, a digital scan converter (DSC) 150, and a control circuit 160. In the present embodiment, the control unit 22 is provided to the ultrasonic image apparatus main body 20, but at least a part of the configuration of the control unit 22 may also be provided to inside the ultrasonic probe 10.

The transmission processing unit 110 performs a process for transmitting ultrasonic waves at a subject. The transmission processing unit 110 has a transmission pulse generator 111 and a transmission delay circuit 113.

The transmission pulse generator 111 applies a transmission pulse voltage and drives the ultrasonic probe 10.

The transmission delay circuit 113 performs a wave transmission focusing control, and causes the ultrasonic probe 10 to emit, at the subject, an ultrasonic beam corresponding to the pulse voltage generated. To that end, the transmission delay circuit 113 creates a time difference between channels with respect to the timing of application of the transmission pulse voltage, and focuses the ultrasonic waves generated from the plurality of vibration elements. In this manner, changing the delay time makes it possible to change the focal length as desired.

In the case of linear scanning, all apertures (referring to the 64 channels in the example illustrated in FIG. 3) are split; transmission and reception are performed at split apertures (usage apertures), and respective lines continue being generated while the usage apertures are being shifted. The usage apertures can be, for example, eight channels. The larger the usage apertures, the narrower the beam width and the greater the azimuth (lateral) resolution. In the case of sector scanning, all apertures are used as usage apertures, and the respective lines continue being generated as the direction of the beam is being varied.

The transmission/reception changeover switch 140 performs a process for switching between transmitting and receiving ultrasonic waves. The transmission/reception changeover switch 140 protects so as to prevent the amplitude pulses for during transmission from being inputted to the reception processing unit 120, and causes the signals for during reception to pass through the reception processing unit 120.

The reception processing unit 120 performs a process for receiving received waves (called "received waves" hereinbelow) of an ultrasonic echo relative to the ultrasonic waves transmitted. The reception processing unit 120 has a reception circuit 121, a filter circuit 123, and a memory 125.

The reception circuit 121 converts the received waves (analog signals) for every channel into digital received signals and outputs the received signals to the filter circuit 123. The focusing control for the received waves is carried out at the image processing unit 130 (described below).

The filter circuit 123 performs filter processing by band pass filter or the like on the received signals for every channel outputted from the reception circuit 121, to remove noise. Then, the received signals for every channel to which the filter processing has been applied are outputted by the filter circuit 123 to the memory 125.

The memory 125 stores for every channel the received signals of every channel outputted from the filter circuit 123. The function of the memory 125 can be realized by making use of a storage apparatus such as a random access memory (RAM).

Figure 6:
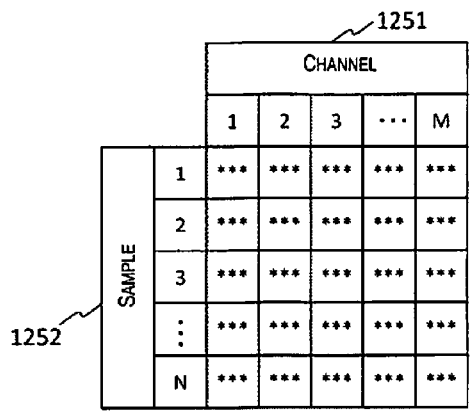
FIG. 6 is a drawing describing one example of the structure of data of each channel stored in a memory.

FIG. 6 is a drawing for describing one example of the structure of the data for each of the channels that is stored in the memory. The memory 125 stores one round of transmission of ultrasonic waves and the received waves of the ultrasonic echo in response thereto as waveform data of a number N of sample received signals with respect to a number M of channels. M is the total number of channels of the usage apertures, and N is the total number of samples. The total number of samples is determined, for example, by a sampling frequency (for example, 50 MHz) prescribed for the ultrasonic image apparatus 1 and the observation time for one round of received waves.

The description now relates again to FIG. 5. The function of the reception processing unit 120 can be realized by, for example, an analog front end (AFC) constituted of a low noise amplifier (LNA), a programmable gain amplifier (PGA), a filter circuit, an analog/digital (A/D) converter, and the like.

The configuration of the reception processing unit 120 is not limited to the example depicted. For example, the filter circuit 123 may be provided between a harmonic processing unit 131 and a minimum variance beamforming (MVB) processing unit 132 and subject the harmonic component of every channel to the filter processing. In such a case, the function of the filter circuit may be implemented with software.

The image processing unit 130 acquires the received signals stored in the memory 125 of the reception processing unit 120 and carries out a variety of image processes. The image processing unit 130 has the harmonic processing unit 131, the MVB processing unit 132, a wave detection processing unit 133, a logarithmic conversion processing unit 135, a gain/dynamic range adjustment unit 137, and a sensitivity time control (STC) 139. The MVB processing unit may also be called a signal processing unit. Those functions out of the functions of the image processing unit 130 that relate to image generation (realized by the wave detection processing unit 133, the logarithmic conversion processing unit 135, the gain/dynamic range adjustment unit 137, and the STC 139) may also be called an image generation unit.

The harmonic processing unit 131 extracts a harmonic component for every channel based on the received signals for every channel stored in the memory 125. The harmonic processing shall be described in greater detail below.

The MVB processing unit 132 performs an MVB process, which is adaptive beamforming where the direction has been constrained, based on the harmonic components of every channel extracted by the harmonic processing unit 131. To that end, the MVB processing unit 132 has a reception focus processing unit 1321, a spatial averaging processing unit 1322, a weight calculation unit 1323, and a weighting addition unit 1324. The MVB process shall be described in greater detail below.

The wave detection processing unit 133 carries out an absolute value (rectification) process on the MVB-processed received signals, and thereafter applies a low-pass filter and extracts unmodulated signals.

The logarithmic conversion processing unit 135 performs a log compression on the extracted unmodulated signals and converts the format of representation so as to facilitation confirming the portions of maximum signal intensity and portions of minimum signal intensity in the received signals at the same time.

The gain/dynamic range adjustment unit 137 adjusts the signal intensity and a region of interest. For example, in a gain adjustment process, a direct current component is added to log-compressed input signals. In a dynamic range adjustment process, the log-compressed input signals are multiplied by any desired number.

The STC 139 corrects the degree of amplification (brightness) in accordance with the depth and acquires an image of uniform brightness over the entire screen.

The function of the image processing unit 130 can be realized by a variety of processors (a CPU or the like), hardware such as an ASIC (a gate array or the like), programs, or the like.

The DSC 150 performs a scan conversion process on B-mode image data. For example, the DSC 150 converts line signals to image signals by a bilinear or other interpolation process. Then, the DSC 150 outputs the image signals to the display unit 21. An image is thereby displayed on the display unit 21.

The control circuit 160 controls the transmission pulse generator 111, the transmission delay circuit 113, the transmission/reception changeover switch 140, the reception circuit 121, the memory 125, the harmonic processing unit 131, and the like.

The configuration of the ultrasonic image apparatus 1 above is where the main components are described when the features of the present embodiment are being described, and is not limited to being the configuration described above. The present invention is in no way limited by the approaches to and names of the classifications of the constituent elements. The configuration of the ultrasonic image apparatus 1 could also be further classified into many constituent elements, depending on the processing content. A single constituent element could also be further classified so as to execute many processes. The processes of each of the constituent elements may be executed with one piece of hardware or may be executed with a plurality of pieces of hardware.

Figure 7:
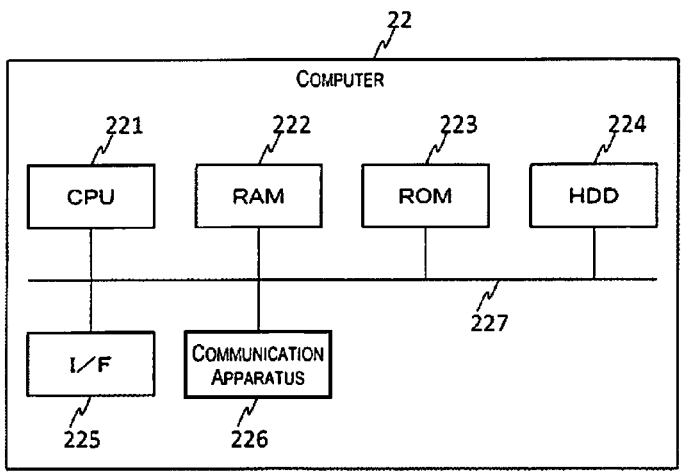
FIG. 7 is a drawing illustrating one example of a hardware configuration for implementing the functions of the control unit.

FIG. 7 is a drawing illustrating one example of a hardware configuration for implementing the functions of the control unit. As illustrated in FIG. 7, the control unit 22 can be implemented by a computer provided with, for example: a central processing unit (CPU) 221, which is a computation apparatus; a random access memory (RAM) 222, which is a volatile storage apparatus; a read-only memory (ROM) 223, which is a non-volatile storage apparatus; a hard disk drive (HDD) 224, an interface (I/F) circuit 225 for connecting the control unit 22 with another unit; a communication apparatus 226 for communicating with an external apparatus; and a bus 227 for connecting these elements to one another.

At least a part of the functions of the control unit 22 described above are realized by when, for example, the CPU 221 reads out to the RAM 222 and executes a predetermined program stored in the ROM 223 or the HDD 224. The predetermined program may be, for example, installed in advance on the ROM 223 or the HDD 224, or may be downloaded from a network via the communication apparatus 226 and then installed or updated.

Next, the harmonic processing shall be described in greater detail. In the present embodiment, the "harmonic processing" refers to a process for extracting a harmonic component in harmonic imaging for the purpose of realizing high resolution in images of ultrasonic echoes.

"Harmonic imaging" refers to a technique for visualizing a harmonic component. Here, the nature of ultrasonic waves (compressional waves) propagating through a medium is such that a portion having high sound pressure moves faster and a portion having low sound pressure moves slower. As such, even with a simple sine wave, distortion is produced in the course of propagation and the waveform changes, and there comes to be included a harmonic component (also called a non-linear component) of an integer multiple of a fundamental frequency that was not included in the fundamental waves (a non-linear effect). This non-linear effect increases in proportion to the square of the sound pressure of the fundamental wave component of the ultrasonic waves, and also accumulates in proportion to the propagation distance.

Harmonic imaging is broadly divided into tissue harmonic imaging, which visualizes the harmonic component that is generated from tissue itself when the ultrasonic waves propagate through the tissue, and contrast harmonic imaging, which visualizes the harmonic component that is generated when microbubbles of an ultrasonic contrast agent resonate and collapse. In the present embodiment, tissue harmonic imaging is used.

There are two advantages to harmonic imaging. A feature of the harmonic component is that the amplitude is proportional to the square of the amplitude of the transmitted ultrasonic waves, and therefore the amplitude of the harmonic component is strong in the middle of the transmitted beam, where the sound pressure is high, but rapidly weakens approaching the ends from the middle of the beam. As a result, in harmonic imaging, the range where the non-linear effect takes place is limited to the middle of the beam, and consequently the azimuth solution is enhanced over other techniques. This is the first advantage.

The main causes of noise that appears in ultrasonic images include noise from multiple reflection and noise from side lobes. Here, the ultrasonic echo that is reflected has a low sound pressure, and the harmonic component itself does not occur. Therefore, noise from multiple reflection is reduced. The side lobes have low sound pressure, and the harmonic component itself does not occur at the side lobes, either. Therefore, noise from the side lobes is also reduced. In this manner, harmonic imaging makes it possible to reduce both noise from multiple reflection and noise from the side lobes. This is the second advantage.

A filter process and/or a phase inversion process is used to extract the harmonic component.

A filter process refers to a technique where a fundamental wave component and a harmonic component are separated by a frequency filter (high-pass filter) and, for example, only a second-order harmonic component is extracted and visualized. A case where the second-order harmonic component is separated and extracted shall now be described by way of example. Where the center frequency of the fundamental wave band is f0 and the center frequency of the second-order harmonic band is 2f0, then the received fundamental wave component and second-order harmonic component each have a respective given bandwidth and therefore the fundamental wave component and the second-order harmonic component overlap and the two can no longer be separated. As a result, the image is degraded. Reducing the overlap between the fundamental wave component and the second-order harmonic component necessitates lengthening the pulse width. When the pulse width is longer, however, then the distance resolution is reduced.

A phase inversion process is a technique developed in order to mitigate the drawbacks of the filter process. This technique comprises twice transmitting ultrasonic waves continuing in the same direction. The second round of transmitted waves has the feature of having a 180° difference in phase relative to the first round of transmitted waves. The received waves that come back after being reflected from a body or contrast agent comprise a harmonic component due to the non-linear propagation properties thereof and therefore become a distorted waveform. Because the transmitted waves are reflected with the first round and with the second round, there is a relationship where the fundamental wave component (first-order) is reflected by the second-order harmonic component is not reflected (in-phase). As a result, when the two rounds of received waves are added, the fundamental wave component is removed and the second-order harmonic component remains, but with a doubled amplitude, and therefore it becomes possible to visualize only the second-order harmonic component. Because it is possible to extract only the second-order harmonic component, broadband transmission becomes possible, and the decline in distance resolution that is a drawback of the filter process is also mitigated.

Now, where even orders of received wave components are represented with $2a$ ($a$ being a natural number 1 or higher) and odd orders are represented with $2a-1$1, then in the first round of received waves and second order of received waves, the components of an order $2a$ are in an in-phase relationship and components of an order $2a-1$ are in a reverse-phase relationship. That is to say, a component of an order $2a$ remains when a process of adding the first round of received waves and the second round of received waves is performed.

Figure 8:
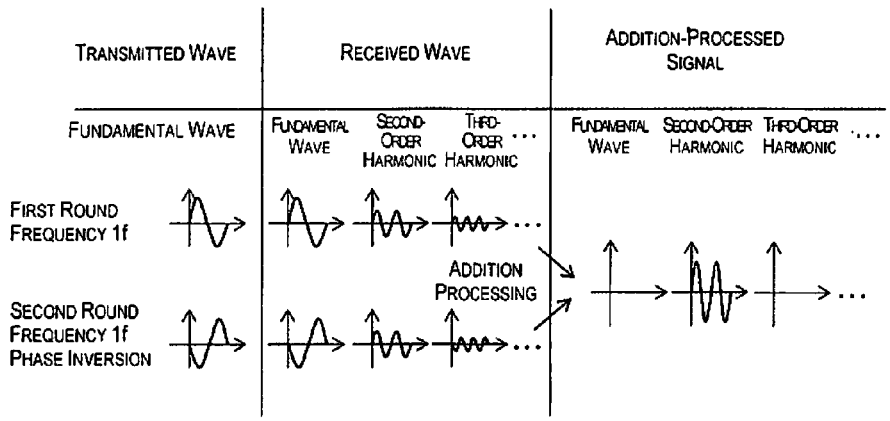
FIG. 8 is a drawing describing one example of a harmonic process performed by an ultrasonic image apparatus.

The present embodiment shall be described understanding the phase inversion process to be used. FIG. 8 is a drawing describing one example of the harmonic processing performed by an ultrasonic image apparatus. As illustrated in FIG. 8, the ultrasonic image apparatus 1 transmits a first ultrasonic pulse of a frequency 1f and a second ultrasonic pulse with which the frequency is 1f and a phase difference with respect to the first ultrasonic pulse is 180° (with which the phase has been inverted), and performs an addition process with the received signals of the first ultrasonic pulse and the received signals of the second ultrasonic pulse, thereby extracting a harmonic of an order $2a$.

Here, as was described with FIG. 6, the total number of channels is understood to be M and the total number of samples is understood to be N. The received signals of an m-th (1st through M-th) channel is represented by xm, and the received signals at a sampling point n (1 through N) in the channel m is represented by xm[n]. The data of the received signals of the first ultrasonic pulse (positive phase) is represented by x_posm[n] and the data of the received signals of the second ultrasonic pulse (reverse phase) is represented with x_negm[n].

The harmonic processing unit 131 adds the data for the received signals of the first ultrasonic pulse and the data for the received signals of the second ultrasonic pulse for every channel to cancel out components of an order $2a-1$ (fundamental waves, third-order harmonic, etc.) and extract components of an order $2a$ (second-order harmonic, fourth-order harmonic, etc.). The harmonic processing unit 131 can use the following formula (1) to find the harmonic component x_Harmonicm[n] of each of the sampling points of each of the channels.

Formula (1)

$$x\_Harmonic_m[n]=x\_pos_m[n]+x\_neg_m[n] \qquad (1)$$

In a case where the filter process is used, then the harmonic component is found by the following formula (2). "filter" represents the filter component.

Formula (2)

$$x\_Harmonic_m[n]=\text{filter}*x_m[n] \qquad (9)$$

Below, for the sake of ease of understanding, the data of each of the channels where the harmonic components have been extracted is represented in a simplified manner, as illustrated by the formula (3).

Formula (3)

$$x_m=x\_Harmonic_m \qquad (3)$$

Next, the MVB process shall be described in greater detail.

First, a conventional beamforming process shall be described for the purpose of comparison with the MVB process. Conventional beamforming is a process for aligning and adding phases of signals of each channel (phasing addition) and amplifying the signals. Only signals with matching phases can be amplified, so the waves that come from a desired direction can be extracted. This is a process equivalent to the Fourier transform.

Here, with conventional beamforming, a weighting addition has been performed using a weight of a fixed value for the signals of each of the channels. For example, a window function such as a rectangular window or Hanning window is used for the weight. A window function changes the shapes of the main lobe and side lobes of the spectrum of the received waves, but the receiving directivity is fixed. The "main lobe" namely refers to the sensitivity to waves in the desired direction, while the "side lobes" refer to the sensitivity to waves coming from elsewhere other than the desired direction. The narrower the main lobe and lower the level of the side lobes, the better the azimuth resolution.

The shapes of the main lobe and the side lobes is determined by the apertures and frequency. When the apertures are infinitely large, then the sensitivity property becomes a delta function, and reception becomes possible only from a specific angle. In practice, finite apertures are used and therefore the occurrence of side lobes is inevitable. When the apertures are the same, then a higher frequency means a narrower main lobe.

Nonetheless, there is still sensitivity to elsewhere other than the desired direction, and waves end up being received, which is a problem. That is to say that the side lobes or alternatively the breadth of the main lobe ends up causing waves from elsewhere other than the desired direction to be received.

For example, with a linear scan, one line image is generated with respect to the perpendicular direction from the apertures. This results in the desire to acquire the reflected signals coming from an object that is present only in front as much as possible (i.e., where the desired direction=0°). Therefore, at the time of transmission, each of the channels is given a delay time, and a transmission beam is transmitted so that the frontal sound pressure is stronger. Ultrasonic waves, however, have the property of spreading out over a sphere, and therefore end up reaching and being reflected at reflectors that are at an angle other than frontal. Therefore, the received signals end up also including unneeded waves from elsewhere other than the desired direction. As stated above, conventional beamforming has reception sensitivity also to unneeded waves that come from elsewhere other than the desired direction, and therefore the azimuth resolution is worsened.

Therefore, in the present embodiment, the MVB process is used. "Adaptive beamforming" refers to a process of dynamically changing the sensitivity characteristic and removing sensitivity to unneeded waves by changing the weights of each of the channels in accordance with the incoming waves. Adaptive beamforming puts a constraint on direction and removes sensitivity to unneeded waves, and therefore makes it possible to mitigate the problem of the decrease in azimuth resolution caused by the unneeded waves. As stated above, the MVB processing unit 132 executes the MVB process on the harmonic components of each of the channels extracted by the harmonic processing unit 131.

More specifically, the reception focus processing unit 1321 applies a delay, of a delay duration Dm defined in advance for each of the channels, to the received signals (harmonic components) of each of the channels so that the signals of each of the channels have aligned phases. Then, the output signal xm of the m-th channel is found with the formula (4). The output signals of each of the channels can also be expressed as in the formula (5).

Formula (4)

$$x_m[n - D_m[n]] \quad (4)$$

Formula (5)

$$X[n] = \begin{bmatrix} x_1[n - D_1[n]] \\ x_2[n - D_2[n]] \\ \vdots \\ x_M[n - D_m[n]] \end{bmatrix} \quad (5)$$

Figure 9:
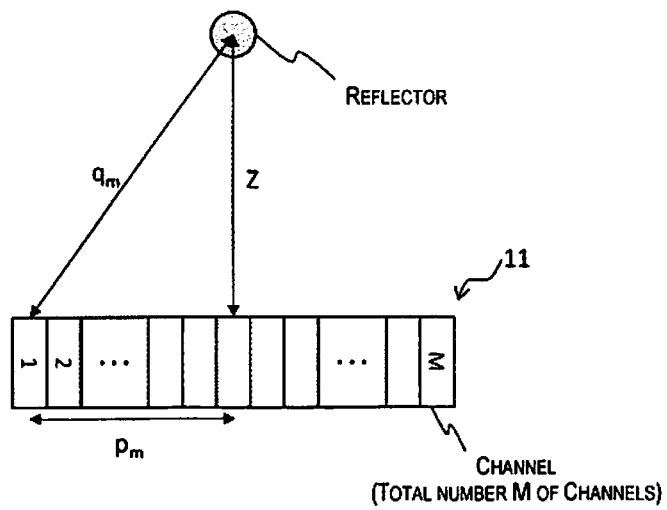
FIG. 9 is a drawing describing the delay of a signal arriving at each channel.

As illustrated in FIG. 9, ultrasonic waves that have been reflected from reflectors that are in a depth direction Z from an ultrasonic transducer device become spherical waves and arrive at the elements of each of the channels. As such, the duration for when the reflected signals arrive at the elements of each of the channels is determined by the linear distance qm from the reflector to the elements of each of the channels; the farther the element is from the reflector, the greater the delay for the ultrasonic waves to arrive. The delay duration Dm is found geometrically as illustrated in the formula (6), and is determined by the position pm of the channel and the depth distance Z. c is the sound velocity (a fixed value).

Formula (6)

$$q_m = \sqrt{p_m^2 + Z^2}$$

$$D_m = q_m/c \quad (6)$$

The reception focus processing is essentially similar to the phase-adjusting process in conventional beamforming.

The output signals calculated with the reception focus processing unit 1321 are outputted to the spatial averaging processing unit 1322 in a case where a spatial averaging process is set to be used. In a case where the spatial averaging process has not been set to be used, then the output signals are outputted to the weight calculation unit 1323 and the weighting addition unit 1324. For the sake of ease of understanding, a case where the spatial averaging process is not used shall be described first.

The weight calculation unit 1323 calculates the weight to be applied to the received signals of each of the channels.

The method of calculating the weight shall now be described. Where "wm" is the weight for each of the channels, then the output z outputted by the weighting addition unit 1324 is the result of multiplying the weight wm of each of the channels and the delay-processed signal xm of each of the channels outputted from the reception focus processing unit 1321 and then the resulting values derived for each channel are added together, and is represented by the formula (7).

Formula (7)

$$z[n] = \sum_{m=1}^{M} w_m[n] x_m[n - D_m[n]] \quad (7)$$

Expressing this formula in vector notation gives the equations (8) and (9). H is the complex conjugate transpose, and * is the complex conjugate.

Formula (8)

$$z[n] = w[n]^H X[n] \quad (8)$$

Formula (9)

$$= \begin{bmatrix} w_1^*[n] \\ w_1^*[n] \\ \vdots \\ w_1^*[n] \end{bmatrix} \quad (9)$$

The correlation matrix R is given by the equations (10) and (11).

Formula (10)

$$R[n] = E[X[n]X[n]^T] \quad (10)$$

Formula (11)

$$E[|z[n]|^2] = w[n]^H R[n] w[n] \quad (11)$$

The equations (10) and (11) are for calculating such a weight as will minimize the dispersion of z[n], and therefore the weight is found as illustrated in the equation (14) when a conditional minimization problem such as is illustrated in equations (12) and (13) is solved.

Formula (12)

$$\min_{w[n]} w[n]^H R[n] w[n] \tag{12}$$

Formula (13)

$$\text{subject to } w[n]^H a = 1 \tag{13}$$

Formula (14)

$$w[n] = \frac{R[n]^{-1} a}{a^H R[n]^{-1} a} \tag{14}$$

Here, a is a steering vector. In the present embodiment, phasing has already been performed, so the direction is 0°. As such, a should be 1.

The weighting addition unit 1324 performs a weighting addition using the weights of each of the channels calculated with the weight calculation unit 1323 and the received signals of each of the channels calculated with the reception focus processing unit 1321. That is to say, a computation according to formula (7) is performed to obtain an output z. The signals calculated with the weighting addition unit 1324 are outputted to the wave detection processing unit 133.

A case where the spatial averaging process is used shall now be described. The spatial averaging processing unit 1322 performs a process called a spatial averaging process, which is processing for taking a plurality of sub-apertures out from the apertures constituted of the M channels and taking the averages respectively. The spatial averaging process is a process that is performed in order to prevent the impact of correlated interference waves from adversely affecting the azimuth estimation accuracy when the values of each of the channels are used directly and without alteration. In place of the spatial averaging process, a process called a time averaging process for taking the average in the time direction of each of the channels may also be performed. The signals having been processed by the spatial averaging processing unit 1322 are outputted to the weight calculation unit 1323 and the weighting addition unit 1324.

Figure 10:
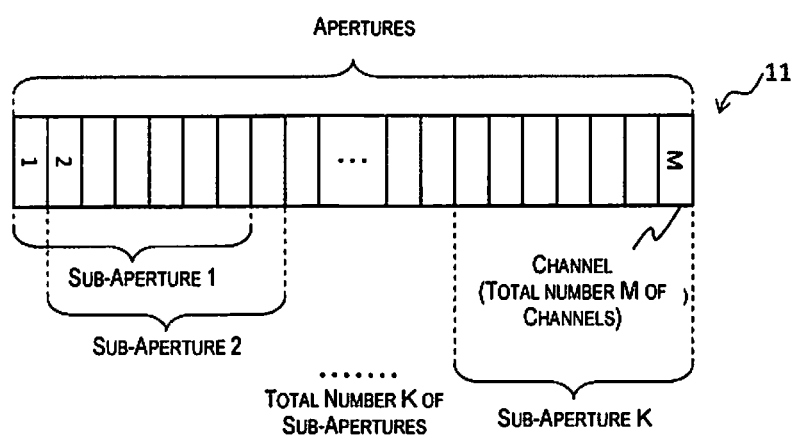
FIG. 10 is a drawing describing a sub-aperture in a spatial averaging process.

A case where a number K of sub-apertures where the number of channels is S (K=M−S+1) are taken out from apertures where the total number of channels is M, as illustrated in FIG. 10, shall now be considered by way of example. In this case, the input vectors of each s-th sub-aperture can be expressed as in the formula (15).

Formula (15)

$$\tilde{x}_s[n] = \begin{bmatrix} x_s[n - D_s[n]] \\ x_{s+1}[n - D_{s+1}[n]] \\ \vdots \\ x_{s+S-1}[n - D_s[n]] \end{bmatrix} \tag{15}$$

The correlation matrix can be expressed as in the formula (16).

Formula (16)

$$\tilde{R}[n] = \frac{1}{M - S + 1} \sum_{s=1}^{M-S+1} \tilde{x}_s[n] \tilde{x}_s^H[n] \tag{16}$$

At this time, the optimal weight is found by the formula (17).

Formula (17)

$$\tilde{w}[n] = \frac{\tilde{R}[n]^{-1} a}{a^H \tilde{R}[n]^{-1} a} \tag{17}$$

The weighting addition unit 1324 performs the weighting addition using the weights of each of the channels calculated with the weight calculation unit 1323 and the received signals of each of the channels calculated with the spatial averaging processing unit 1322. Namely, a computation according to the formula (18) is performed and an output z is obtained. The signals calculated with the weighting addition unit 1324 are outputted to the wave detection processing unit 133.

Formula (18)

$$z[n] = \frac{1}{M - S + 1} \sum_{s=1}^{M-S+1} \tilde{w}[n]^H \tilde{x}_s[n] \tag{18}$$

Next, the flow of the operation implemented by the ultrasonic image apparatus shall be described.

FIGS. 11 to 14 are flowcharts (a first through fourth) illustrating one example of the processing implemented by the ultrasonic image apparatus. The flowcharts in FIGS. 11 to 14 illustrate the flow by which an image amounting to one frame is generated.

First, the control circuit 160 initializes a scan line number l, which is an ordinal number indicative of the line at which an image is generated, to 1 (l=1) (step S100). The scan line number l is an ordinal number indicative of which one is the element group out of the ultrasonic transducer element groups UG1 to UG64 that constitute the ultrasonic transducer device such as is illustrated in FIG. 3. For example, "1" is the scan line number l for the element group provided to any end, referring here to the ultrasonic transducer element group UG1. "2", then, is the scan line number l for the element group adjacent to the element group of the scan line number "1", referring here to the ultrasonic transducer element group UG2. Scan line numbers l are allocated to all of the element groups in this manner. The relationships between the ultrasonic transducer element groups UG1 to UG64 and the scan line numbers l should be stored in a memory such as a ROM.

Next, the control circuit 160 performs transmission and reception of an ultrasonic pulse with a frequency 1f and phase 0° via all of the channels of the usage apertures corresponding to the scan line number l initialized in step S100 or a scan line number l that has been updated in a step S128 described below (steps S101 to S106). For example, the channels of the usage apertures for when the scan line number is "1" are the ultrasonic transducer element groups UG1 to UG8, and the channels of the usage apertures for when the scan line number is "2" are the ultrasonic transducer element groups UG2 to UG9. The relationships between the scan line numbers and the channels of the corresponding usage apertures should be stored in a memory such as a ROM.

The transmission pulse generator 111 generates a pulse voltage for transmitting the ultrasonic pulse with a frequency 1f and a pulse 0° (step S101). The transmission delay circuit 113 performs the wave transmission focusing control (step S102), and the ultrasonic probe 10 emits at a subject an ultrasonic beam corresponding to the pulse voltage generated in step S101 (step S103).

The control circuit 160 performs a changeover between transmission and reception via the transmission/reception changeover switch 140. The ultrasonic probe 10 receives at all of the channels of the usage apertures the received waves that come back after the emitted ultrasonic beam is reflected at the subject, and the signals received are passed to the reception processing unit 120. The reception circuit 121 converts the received waves (analog signals) of every channel of the usage apertures to digital received signals, and the digital received signals are outputted to the filter circuit 123 (step S104).

The filter circuit 123 performs a bandpass filter process on the received signals of every channel of the usage apertures (step S105). The control circuit 160 saves the received signals of every channel of the usage apertures that are outputted from the filter circuit 123 into the memory 125 (step S106).

Next, the control circuit 160 performs transmission and reception of an ultrasonic pulse with a frequency 1f and phase 180° via all of the channels of the usage apertures corresponding to the scan line number l initialized in step S100 or a scan line number l that has been updated in a step S128 described below (steps S111 to S116; see FIG. 9). That is to say, in the steps S111 to S116, the control circuit 160 transmits and receives an ultrasonic pulse with a phase difference of 180° (inverted phase) with respect to the ultrasonic pulse that was transmitted and received in the steps S101 to S106.

The transmission pulse generator 111 generates a pulse voltage for transmitting the ultrasonic pulse with a frequency 1f and a phase 180° (step S111). The transmission delay circuit 113 performs the wave transmission focusing control (step S112), and the ultrasonic probe 10 emits at the subject an ultrasonic beam corresponding to the pulse voltage generated in step S111 (step S113). The process in step S114 is the same as in step S104, the process in step S115 is the same as in step S105, and the process in step S116 is the same as in step S106, and therefore a description thereof is omitted.

Next, the control circuit 160 issues an instruction to the harmonic processing unit 131, and the harmonic processing unit 131 acquires the positive-phase received signals saved in the memory 125 in step S106 and the reverse-phase received signals saved in the memory 125 in step S116 for every channel of the usage apertures, and extracts the harmonic components by running the addition processing on these acquired received signals (step S121). The details therein are as is described above.

Next, the MVB processing unit 132 performs the MVB processing, which is adaptive beamforming that puts a constraint on direction, based on the harmonic components of every channel of the usage apertures extracted by the harmonic processing unit 131 in step S121 (step S122). The details therein are as is described above. That is to say, the reception focus processing unit 1321 runs the delay processing defined in advance for each of the channels on the harmonic components of each of the channels, and the spatial averaging processing unit 1322 performs the spatial averaging process on the signals on which the reception focus processing unit 1321 has run the delay processing. The weight calculation unit 1323 calculates the weight for each of the channels and the weighting addition unit 1324 uses the calculated weights to add the weightings to the signals of each of the channels.

Next, the wave detection processing unit 133 applies the low-pass filter after the absolute value (rectification) processing to the harmonic components for the scan line number l outputted by the MVB processing unit 132 in step S122, to extract the unmodulated signals (i.e., performs an envelope detection) (step S123). Then, the logarithmic conversion processing unit 135 performs the logarithmic conversion processing (step S124).

Then, the gain/dynamic range adjustment unit 137 adjusts the signal intensity and region of interest (step S125). Then, the STC 139 corrects the degree of amplification (brightness) in accordance with the depth (step S126).

Next, the control circuit 160 determines whether or not the scan line number l, which is the ordinal number indicative of the line at which the image is generated, is smaller than a number of scan lines L (step S127). The number of scan lines L is the number of ultrasonic transducer element groups UG1 to UG64 in the case of the ultrasonic transducer device such as is illustrated in FIG. 3.

Figure 11:
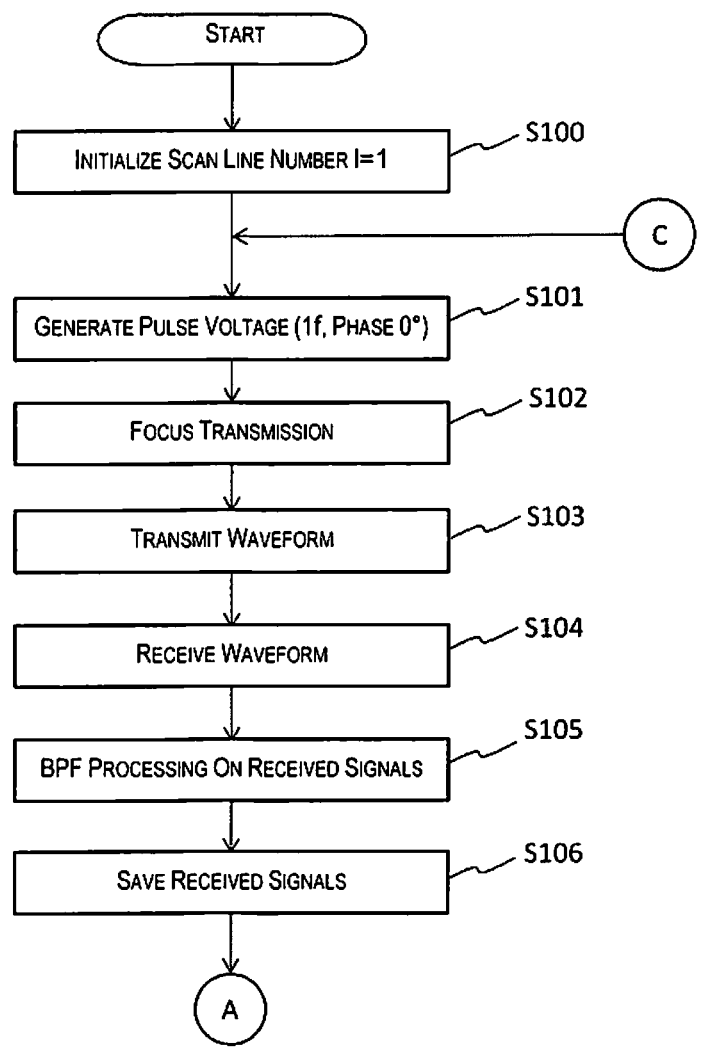
FIG. 11 is a (first) flowchart illustrating one example of a process implemented by an ultrasonic image apparatus.
Figure 12:
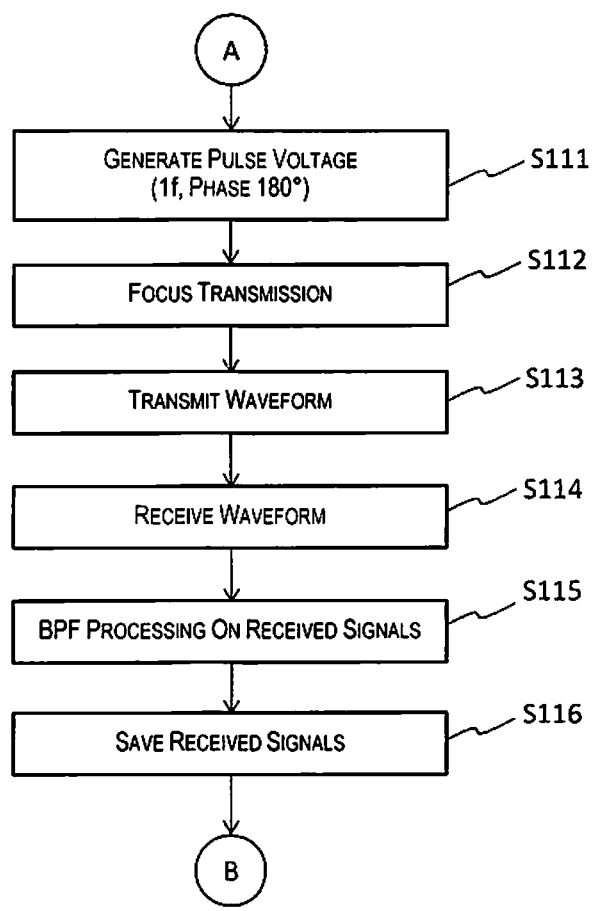
FIG. 12 is a (second) flowchart illustrating one example of a process implemented by an ultrasonic image apparatus.
Figure 13:
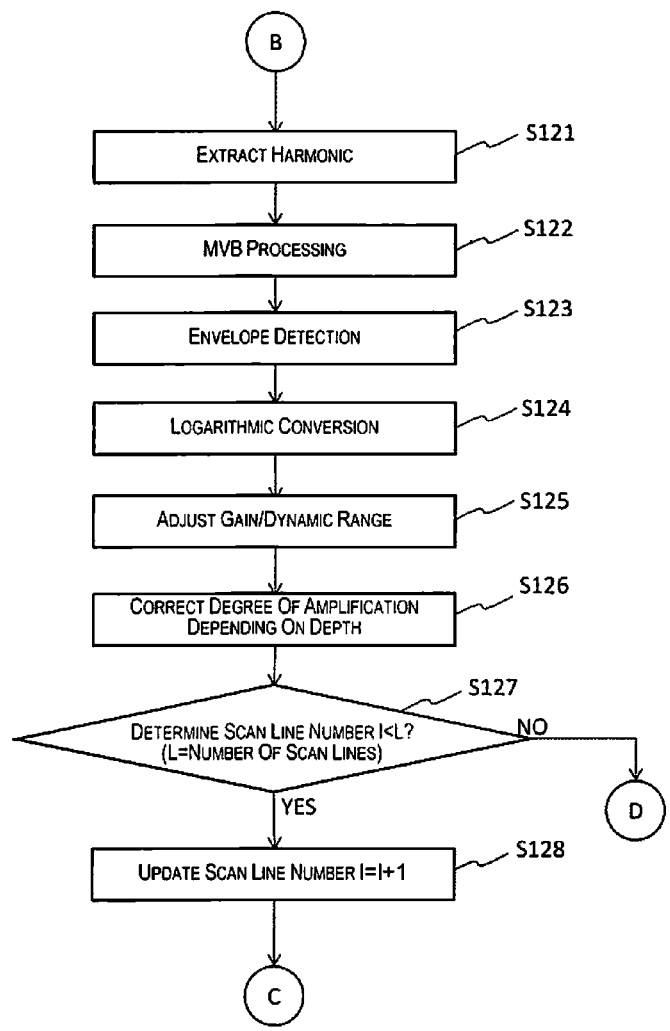
FIG. 13 is a (third) flowchart illustrating one example of a process implemented by an ultrasonic image apparatus.
Figure 14:
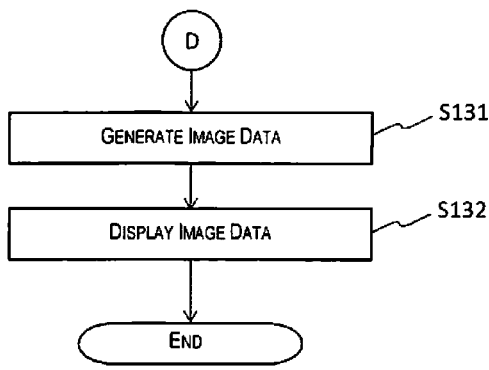
FIG. 14 is a (fourth) flowchart illustrating one example of a process implemented by an ultrasonic image apparatus.

In a case where the scan line number l is smaller than the number of scan lines L (YES in step S127), then the control circuit 160 adds "1" to the scan line number l to update the scan line number l (step S128). Then, the processing returns to step S101 (FIG. 11).

In a case where the scan line l is not smaller than the number of scan lines L (NO in step S127) (i.e., a case where the scan line number l matches the number of scan lines L), however, then: the control circuit 160 issues an instruction to the image processing unit 130; the image processing unit 130 generates a frame image from the signals of all of the scan lines processed in steps S121 to step S126; and the processing is advanced to step S131.

The DSC 150 performs a scan conversion process based on the signals (frame image) of all of the scan lines generated by the image processing unit 130, and generates B-mode image data (display image data) that is outputted to the display unit 21 (step S131). The display unit 21 displays the display image data thus generated (step S132). This completes the processing of the flowcharts illustrated in FIGS. 11 to 14.

Finally, the B-mode image that is displayed by an ultrasonic image apparatus to which the present embodiment has been applied and the B-mode image that is displayed by an ultrasonic image apparatus shall be compared.

Ultrasonic image apparatuses having the following functions (A) to (D) were run through a simulation in the same environment. (A) to (C) correspond to the prior art and (D) corresponds to the present embodiment.

(A) The fundamental wave component is acquired from received waves of an ultrasonic echo with regard to an ultrasonic wave of a predetermined frequency transmitted at a test subject, and the B-mode image is generated based on the acquired fundamental wave component. (B) The harmonic components are acquired from received waves of an ultrasonic echo with regard to an ultrasonic wave of a predetermined frequency transmitted at a test subject, and the B-mode image is generated based on the acquired harmonic components. (C) The fundamental wave component is acquired from received waves of an ultrasonic echo with regard to an ultrasonic wave of a predetermined frequency transmitted at a test subject, and the acquired fundamental wave component is subjected to adaptive beamforming to generate the B-mode image.

(D) The harmonic components are acquired from received waves of an ultrasonic echo with regard to an ultrasonic wave of a predetermined frequency transmitted at a test subject, and the acquired harmonic components are subjected to adaptive beamforming to generate the B-mode image.

Figure 15:
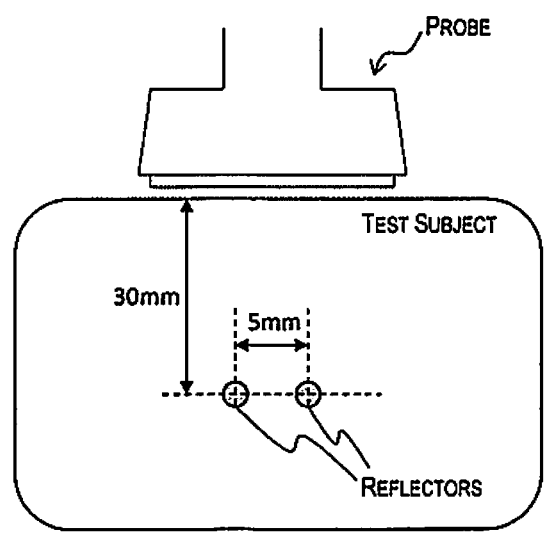
FIG. 15 is a drawing describing a simulation environment relating to the display of a B-mode image.

FIG. 15 is a drawing describing the simulation environment relating to the display of the B-mode images. As illustrated in FIG. 15, the test subject has been examined by an ultrasonic probe. Arranged in the interior of the test subject are two reflectors, spaced apart by a 5-mm gap at positions 30 mm deep from the surface thereof.

Figures 16A, 16B:
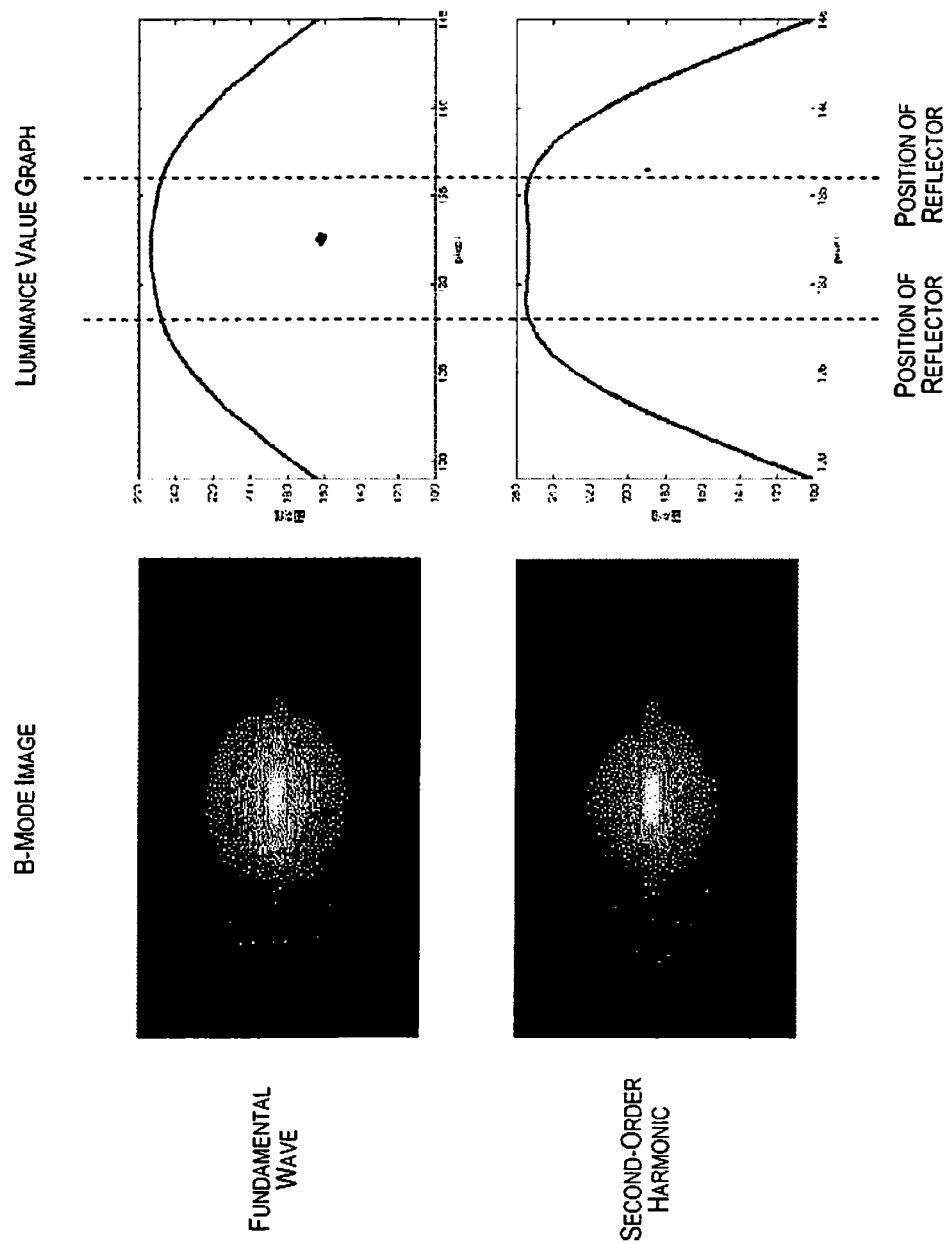
FIGS. 16A and 16B are drawings describing a (first) result of a simulation relating to the display of a B-mode image.

FIGS. 16A and 16B are drawings describing the (first) results of a simulation relating to the displaying of the B-mode images. FIGS. 17A and 17B are drawings describing the (second) results of a simulation relating to the displaying of the B-mode images. FIG. 16A is the simulations results for the conventional ultrasonic image apparatus (A). FIG. 16B is the simulation results for the conventional ultrasonic image apparatus (B). FIG. 17C is the simulation results for the conventional ultrasonic image apparatus (C). FIG. 17D is the simulation results for the ultrasonic image apparatus (D) corresponding to the present embodiment.

The conventional ultrasonic image apparatus (C) has an improvement in the azimuth resolution compared to the conventional ultrasonic image apparatus (A) and the conventional ultrasonic image apparatus (B), as is clear from the displayed examples of B-mode images and luminance value graphs illustrated in FIGS. 16 to 17. Then, the ultrasonic image apparatus (D) has further improvement in the azimuth resolution compared to the conventional ultrasonic image apparatus (C).

An embodiment of the present invention has been described above. According to the present embodiment, an image with higher resolution can be obtained while adaptive beamforming is being applied to an ultrasonic image apparatus.

That is to say, in the present embodiment, adaptive beamforming was applied to harmonic components extracted with harmonic processing. This makes it possible to obtain an image with enhanced azimuth resolution. As a result, adaptive beamforming can be applied to an ultrasonic image apparatus so as to be able to meet the needs of practical use. Because a harmonic is a small signal that occurs in the course of propagation of ultrasound, the S/N ratio is poor, but noise can be suppressed by adaptive beamforming. When the harmonics are being taken out, false signals sometimes occur due to phase shift or the like, but can be suppressed by adaptive beamforming.

The present invention has been described above using the embodiment, but the technical scope of the present invention is not limited to being the scope set forth in the embodiment described above. It shall be readily understood by a person skilled in the art that a variety of modifications or improvements could be added to the embodiment described above. The claims also make it clear that a mode where such a modification or improvement has been added could also be included within the technical scope of the present invention. The present invention is not limited to be an ultrasonic image apparatus, but could also be provided in a variety of different modes such as a method of image processing for an ultrasonic image apparatus, a program for an ultrasonic image apparatus, or a storage medium storing this program. The present invention could also be provided as an ultrasonic measurement apparatus with which the ultrasonic image apparatus main body 20 and the display image data generated is outputted to an external display unit. The present invention could furthermore be provided in a variety of modes such as a method of image processing for an ultrasonic measurement apparatus, a program for an ultrasonic measurement apparatus, or a storage medium storing this program. In the present invention, without including the ultrasonic probe, the ultrasonic image apparatus main body may also be called the ultrasonic image apparatus and the ultrasonic measurement apparatus main body may be called the ultrasonic measurement apparatus.

The present invention can also be applied to any format of scanning, such as linear scanning where the apertures of a probe are split and lines are generated by the sub-apertures, sector scanning where an ultrasonic beam is angled by adjusting the delay duration of each of the channels, or offset sector scanning that is used for convex-shaped probes. The present invention could also be applied even with a format of scanning where transmission and reception are not performed for every line, called aperture synthesis.

GENERAL INTERPRETATION OF TERMS

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An ultrasonic measurement apparatus comprising:
   a receiver configured to receive a plurality of ultrasonic echoes at different incident angles, the ultrasonic echoes corresponding to an ultrasonic wave transmitted toward a subject and containing fundamental wave components and harmonic components;
   a harmonic processor configured to extract a second or higher-order harmonic component signal of each of the ultrasonic echoes;

a signal processor configured to perform minimum variance beamforming process only to the extracted harmonic component signals by applying to the extracted harmonic component signals respective weights, which vary according to incident angles of the ultrasonic echoes to reduce sensitivity to the ultrasonic echoes received from directions other than a direction of a main lobe of the transmitted ultrasonic wave; and an image processor configured to generate an image based on the resulting harmonic component signals.

2. The ultrasonic measurement apparatus as set forth in claim 1, wherein
the receiver comprises an ultrasonic element array having a plurality of channels, one or more of the plurality of ultrasonic echoes at different incident angles being received through each of the channels.

3. The ultrasonic measurement apparatus as set forth in claim 2, wherein
the signal processor processes the harmonic component signals of each channel serially.

4. The ultrasonic measurement apparatus as set forth in claim 1, wherein
the signal processor is configured to perform a spatial averaging process to the harmonic component signals before applying the weights.

5. The ultrasonic measurement apparatus as set forth in claim 1, further comprising:
a filter configured to remove noise from the extracted harmonic component signals.

6. The ultrasonic measurement apparatus as set forth in claim 1, wherein
two ultrasonic waves are transmitted, the two ultrasonic waves having a phase difference of 180° at a predetermined frequency, and
the harmonic processor adds the ultrasonic echoes corresponding to the two ultrasonic waves.

7. The ultrasonic measurement apparatus as set forth in claim 1, wherein
the harmonic processor is configured to extract the harmonic component signals by performing a filter process.

8. An ultrasonic image apparatus comprising:
the ultrasonic measurement apparatus of claim 1; and
a display configured to display the generated image.

9. An ultrasonic measurement method comprising:
receiving, by a receiver, a plurality of ultrasonic echoes at different incident angles, the ultrasonic echoes corresponding to an ultrasonic wave transmitted toward a subject and containing fundamental wave components and harmonic components;

extracting, by a harmonic processor, a second or higher-order harmonic component signal of each of the ultrasonic echoes;

performing minimum variance beamforming process only to the extracted harmonic component signals, by a signal processor, by applying to the extracted harmonic component signals respective weights, which vary according to incident angles of the ultrasonic echoes to reduce sensitivity to the ultrasonic echoes received from directions other than a direction of a main lobe of the transmitted ultrasonic wave; and generating, by an image processor, an image based on the resulting harmonic component signals.

10. The ultrasonic measurement apparatus as set forth in claim 1, wherein
the direction of the main lobe of the transmitted ultrasonic wave is a frontal direction of the receiver.

11. The ultrasonic measurement apparatus as set forth in claim 2, wherein
the signal processor is configured to perform the minimum variance beamforming process by calculating the respective weights to be applied to the extracted harmonic component signals of the ultrasonic echoes received through each of the channels such that a dispersion of sums of resulting values derived from multiplying each of the respective weights and the harmonic component signal of a corresponding one of the channels is minimized.

* * * * *